United States Patent [19]
Bellotti et al.

[11] Patent Number: 5,527,472
[45] Date of Patent: Jun. 18, 1996

[54] CLOSED SYSTEMS AND METHODS FOR REMOVING UNDESIRED MATTER FROM BLOOD CELLS

[75] Inventors: Marc Bellotti, Libertyville; Daniel M. Karlovsky, Arlington Heights; Samira E. Johnson, Lake Zurich, all of Ill.

[73] Assignee: Baxter International Inc., Deerfield, Ill.

[21] Appl. No.: 77,288

[22] Filed: Jun. 14, 1993

[51] Int. Cl.$^6$ .............................. B01D 37/00; B01D 39/00
[52] U.S. Cl. ......................... 210/767; 210/120; 210/194; 210/195.1; 210/252; 210/257.1; 210/258; 210/435; 210/446; 210/749; 210/806
[58] Field of Search ........................... 210/749, 767, 210/782, 787, 805, 806, 97, 120, 188, 194, 195.1, 201, 202, 206, 218, 254, 257.1, 258, 295, 360.1, 361, 435, 436, 446, 472, 252; 604/4, 5, 406, 408, 410; 422/41, 44, 72; 494/20, 21

[56] References Cited

U.S. PATENT DOCUMENTS

| | | | |
|---|---|---|---|
| 4,396,382 | 8/1983 | Goldhaber | 604/410 |
| 4,439,179 | 3/1984 | Lueders et al. | 604/34 |
| 4,767,541 | 8/1988 | Wisdom | 210/749 |
| 4,997,577 | 3/1991 | Stewart | 210/767 |
| 5,092,996 | 3/1992 | Spielberg | 604/406 |
| 5,126,054 | 6/1992 | Matkovich | 210/641 |
| 5,128,048 | 7/1992 | Stewart et al. | 210/749 |
| 5,180,504 | 1/1993 | Johnson et al. | 210/767 |
| 5,217,627 | 6/1993 | Pall et al. | 210/782 |
| 5,269,946 | 12/1993 | Goldhaber et al. | 604/406 |

Primary Examiner—John Kim
Attorney, Agent, or Firm—Daniel D. Ryan; Bradford R. L. Price; Joseph B. Barrett

[57] ABSTRACT

Systems and methods for processing blood direct blood through the inlet of a separation device for removing undesired matter while directing the blood substantially free of undesired matter from the outlet of the separation device and into a collection container through the first port. The systems and methods expel residual air from the collection container through a second port different than the first port. The systems and methods direct the residual air toward the inlet of the separation device to move residual blood from the separation device for collection in the collection container through the first port,

7 Claims, 7 Drawing Sheets

CLOSED SYSTEMS AND METHODS FOR REMOVING UNDESIRED MATTER FROM BLOOD CELLS

FIELD OF THE INVENTION

The invention generally relates to blood collection and processing systems and methods. In a more particular sense, the invention relates to systems and methods for removing white blood cells from red blood cells prior to transfusion or long term storage.

BACKGROUND OF THE INVENTION

Most of the whole blood collected from donors today is not itself stored and used for transfusion. Instead, the whole blood is separated into its clinically proven components (typically red blood cells, platelets, and plasma), which are themselves individually stored and used to treat a multiplicity of specific conditions and diseased states. For example, the red blood cell component is used to treat anemia; the concentrated platelet component is used to control thrombocytopenic bleeding; and the platelet-poor plasma component is used as a volume expander or as a source of Clotting Factor VIII for the treatment of hemophilia.

Systems composed of multiple, interconnected plastic bags have met widespread use and acceptance in the collection, processing and storage of these blood components. In the United States, these multiple blood bag systems are subject to regulation by the government. For example, the plastic materials from which the bags and tubing are made must be approved by the government. In addition, the maximum storage periods for the blood components collected in these systems are prescribed by regulation.

In the United States, whole blood components collected in a nonsterile, or "open", system (i.e. one that is open to communication with the atmosphere) must, under governmental regulations, be transfused within twenty-four hours. However, when whole blood components are collected in a sterile, or "closed", system (i.e., one that is closed to communication with the atmosphere), the red blood cells can be stored up to forty-two days (depending upon the type of anticoagulant and storage medium used); the platelet concentrate can be stored up to five days (depending upon the type of storage container); and the platelet-poor plasma may be frozen and stored for even longer periods. Conventional systems of multiple, interconnected plastic bags have met with widespread acceptance, because these systems can reliably provide the desired sterile, "closed" environment for blood collection and processing, thereby assuring the maximum available storage periods.

In collecting whole blood components for transfusion, it is desirable to minimize the presence of impurities or other materials that may cause undesired side effects in the recipient. For example, because of possible febrile reactions, it is generally considered desirable to transfuse red blood cells substantially free of the white blood cell components, particularly for recipients who undergo frequent transfusions.

One way to remove white blood cells is by washing the red blood cells with saline. This technique is time consuming and inefficient, as it can reduce the number of red blood cells available for transfusion. The washing process also exposes the red blood cells to communication with the atmosphere, and thereby constitutes a "non-sterile" entry into the storage system. Once a non-sterile entry is made in a previously closed system, the system is considered "opened", and transfusion must occur within twenty-four hours, regardless of the manner in which the blood was collected and processed in the first place. In the United States, an entry into a blood collection system that presents the probability of non-sterility that exceeds one in a million is generally considered to constitute a "non-sterile" entry.

Another way to remove white blood cells is by filtration. Systems and methods for accomplishing this within the context of conventional multiple blood bag configurations are described in Wisdom U.S. Pat. Nos. 4,596,657 and 4,767,541, as well as in Carmen et al U.S. Pat. Nos. 4,810,378 and 4,855,063. In these arrangements, an inline white blood cell filtration device is used. The filtration can thereby be accomplished in a closed system. However, the filtration processes associated with these arrangements require the extra step of wetting the filtration device before use with a red blood cell additive solution or the like. This added step complicates the filtration process and increases the processing time.

Other systems and methods for removing white blood cells in the context of closed, multiple blood bag configurations are described in Stewart U.S. Pat. Nos. 4,997,577 and Stewart et al. 5,128,048. In these filtration systems and methods, a transfer assembly dedicated solely to the removal of white blood cells from red blood cells is used. The transfer assembly also has a second fluid path that bypasses the separation device for the purpose of transporting liquid and air around the separation device.

A need still exists for further improved systems and methods for removing undesired matter from blood components prior to transfusion or storage in a way that lends itself to use in closed multiple blood bag system environments.

SUMMARY OF THE INVENTION

The invention provides a multiple container blood collection system for conveniently processing the various components of blood.

The systems and methods that embody the features of the invention are particularly well suited for use in association with closed blood collection systems and conventional sterile connection techniques, thereby permitting separation to occur in a sterile, closed environment.

One aspect of the invention provides a blood processing system and associated method that include an integral, inline separation device for removing undesired matter from blood. The system and method also include a collection container having separate first and second ports.

The system and method direct blood through the inlet of the separation device to remove undesired matter. The system and method also direct the blood substantially free of undesired matter from the outlet of the separation device into the collection container through the first port.

The system and method expel residual air from the collection container through the second port. The system and method use this residual air to flush residual blood from the separation device and into the collection container.

More particularly, the system and method direct the residual air expelled from the second port of the collection container toward the inlet of the separation device. The residual air moves residual blood from the separation device into the collection container through the first port.

This aspect of the invention vents residual air from the collection container through a path that not only bypasses the separation device, but a path that also is kept free from contact with blood throughout the blood separation and collection process. The invention thereby avoids the necessity of sterile vents or other complicated venting schemes to eliminate residual air in a closed blood processing system.

This aspect of the invention also circulates the vented air back toward the inlet of the separation device to flush residual blood from the separation device and into the collection container. The invention thereby avoids waste and maximizes to the fullest extent possible the yields obtained during processing.

According to another aspect of the invention, once expelling residual air from the collection container, the system and method seal the air vent path. The system and method then transfer a small aliquot or sample of the collected blood in the sealed vent path. The sealed vent path serves as a sample tube to retain a blood sample for later crossmatching and typing purposes. The sample tube, continuously integrally attached to the collection container, preserves a direct link between the donor's blood sample and the blood component stored in the collection bag.

According to this aspect of the invention, the system and method retain the blood sample in a portion of tubing that beforehand serves only to transfer air, and is thereby kept free of prior contact with blood. The system and method thus eliminate the chance of contaminating the relatively small sample of processed blood through contact with disproportionately larger concentrations of other blood elements that might be created during one of the previous processing steps.

According to another aspect of the invention, the system and method mix an additive solution with the blood in a mixing container before separating the undesired matter from it. In this aspect of the invention, the mixing container is also used to collect the residual air expelled from the collection container. The collected residual air is directed from the mixing container to flush residual blood (now mixed with the additive solution) from the separation device.

Another aspect of the invention provides a blood processing system having a first container and a second container. Transfer tubing integrally connects the first and second containers. The transfer tubing includes an integral, inline separation device for removing undesired matter from the blood during transfer between the first and second containers. The system is intended to undergo centrifugation as an integral unit within a conventional centrifuges bucket. During centrifugation, blood in the first container separates into component parts.

This aspect of the invention provides a flexible pouch for holding the separation device during centrifugation within the bucket. The separation device nests within the pouch in between the first and second containers inside the centrifuge bucket. The pouch presents a relatively thin, flat profile and does not significantly add to the volume and weight of system during centrifugation. It creates a protective interface between the separation device and the containers during centrifugation, shielding the containers from direct contact against the separation device. In this way, the pouch protects the containers from puncture or damage during processing within the bucket.

While the systems and methods that embody the features of the invention can be used to process all types of blood components, they are well suited for the removal of white blood cells from red blood cells by filtration prior to transfusion or long term storage.

Other features and advantages of the invention will become apparent upon review of the following description, drawings, and appended claims.

BRIEF DESCRIPTION OF THE DRAWINGS

FIG. 2 is a schematic view of the assembly shown in FIG. 1 when used to transfer plasma component and RBC component to associated transfer bags;

FIG. 9 is an enlarged perspective view of the ballast bag outside the centrifuge bucket.

DESCRIPTION OF THE PREFERRED EMBODIMENTS

Figure 1:
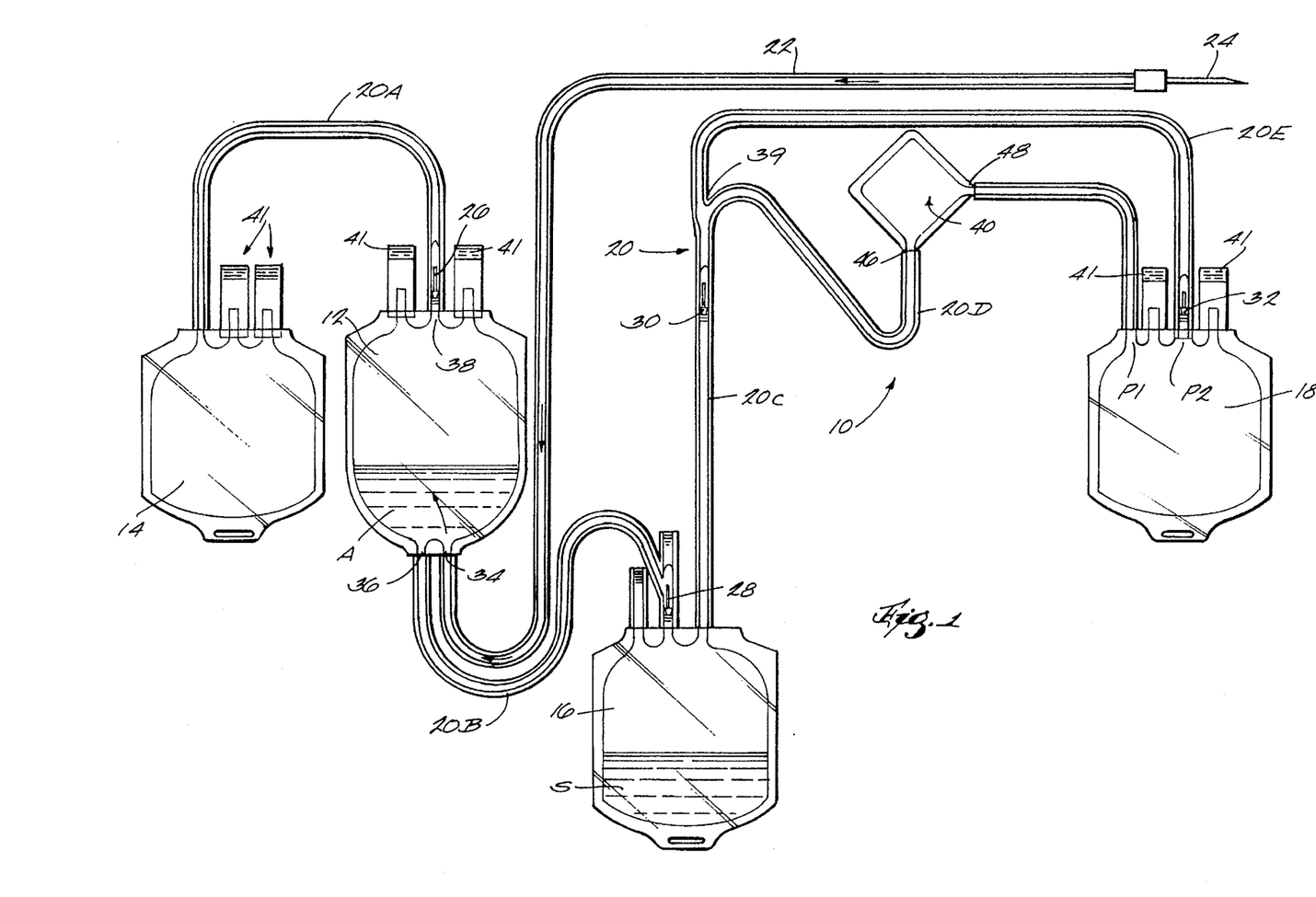
FIG. 1 is a schematic view of a blood collection assembly that embodies the features of the invention.

A blood collection assembly 10 is shown in FIG. 1. In the illustrated embodiment, the assembly 10 serves to separate and store the red blood cells as well as the plasma and platelet blood components by conventional centrifugation techniques. The assembly 10 also serves to remove undesired matter from the red blood cells before storage. In the illustrated embodiment, the undesired matter is removed by filtration.

As used herein, the term "filtration" is intended to include separation achieved by various centrifugal and non-centrifugal techniques, and not merely "filtration" in the technical sense. Separation can occur by absorption, columns, chemical, electrical, and electromagnetic means. The term "filtration" is thus broadly used in this specification to encompass all of these separation techniques as well.

In the illustrated and preferred embodiment shown in FIG. 1, the assembly 10 includes a primary bag or container 12 and several transfer bags or containers 14, 16, and 18. The primary bag 12 includes an integrally attached donor tube 22 that carries a phlebotomy needle 24.

Branched tubing 20 integrally attaches the primary bag 12 to the transfer bags 14, 16, and 18. The tubing 20 is divided into tube branches 20A; 20B; 20C; 20D; and 20E.

In the illustrated embodiment, the assembly 10 includes in line fluid flow control devices 26; 28; 30; and 32 in the tube branches 20A; 20B; 20C; 20D; and 20E. In the illustrated arrangement, the flow control devices take the form of conventional frangible cannulas. Each cannula normally blocks fluid flow through its associated tube branch. When manually bent, the cannula breaks apart to open the associated tube branch.

In the illustrated embodiment, the cannula 26 controls fluid flow through the branch tube 20A. The cannula 28 controls fluid flow through the branch tube 20B. The cannula 30 controls fluid flow through the branch tubes 20C and 20D. The cannula 32 controls fluid flow through the branch tube 20E.

In the illustrated and preferred embodiment, the primary bag 12 has a top and bottom port configuration like that described and claimed in Johansson et al U.S. Pat. No. 4,608,178. A commercial embodiment of such a system is sold by Baxter Healthcare Corporation (Fenwal Division) under tradename OPTI-SYSTEM. It should be appreciated that, alternatively, the all the ports associated with the primary bag can be arranged along the top of the bag, as is also conventional for blood bags.

In the particular configuration shown in FIG. 1, the bag 12 includes two bottom ports 34 and 36 and a top port 38. The branch tube 20B communicates with the bottom port 34. The donor tube 22 communicates with the bottom port 36. The branch tube 20A communicates with the top port 38.

In the illustrated embodiment, the primary bag 12 and the transfer bags 14 and 18 include normally sealed administration ports 41. The ports 41 are enclosed within conventional tear-away flaps. When opened, the flaps expose the ports 40 for attachment to conventional transfusion or transfer tubing (not shown).

In use, the primary bag 12 receives whole blood from a donor through the integrally attached donor tubing 22 (as the arrows in FIG. 1 show). The primary bag 12 contains a suitable anticoagulant A.

The whole blood undergoes separation by centrifugation within the primary bag 12. The centrifugation separates the whole blood into various cellular and non-cellular components.

In use, the transfer bag 14 is intended to receive the plasma blood component of the whole blood collected in the primary bag 12 through branch tube 20A. The transfer bag 14 ultimately serves as the storage container for the plasma blood component.

Depending upon the particular objectives of the blood processing procedure, the plasma component can carry substantially all the platelets associated with the collected whole blood, in which case the component would be called "platelet-rich plasma" or PRP. Alternatively, the plasma component can be substantially free of platelets, in which case the component would be called "platelet-poor plasma" or PPP.

In the illustrated embodiment, the transfer bag 16 contains a storage solution S for the red blood cell (RBC) component of the whole blood collected in the primary bag 12. One such solution is disclosed in Grode et al U.S. Pat. No. 4,267,269. Another such solution is conventionally called "SAG-M" solution.

In use, the transfer bag 16 receives the separated RBC component through the branch tube 20B. The separated RBC component is mixed with the storage solution S in the bag 16. For this reason, the transfer bag 16 can also be called a mixing bag.

Branch tubes 20C and 20D together form a flow path between the transfer bag 16 and the transfer bag 18. The branch tube 20D communicates with the transfer bag 18 through a first port P1.

This branch tube 20D includes an inline separation device 40 for separating undesired matter from blood cells. The separation device 40 includes an inlet 46 and an outlet 48.

In use, the transfer bag 18 receives the RBC component through the first port P1 (mixed with the storage solution S) after passage through the separation device 40. The transfer bag 18 ultimately serves as the storage container for the RBC component.

The bags and tubing associated with the processing assembly 10 can be made from conventional approved medical grade plastic materials, such as polyvinyl chloride plasticized with di-2-ethylhexylphthalate (DEHP). As FIG. 1 shows, a conventional "Y" or "T" connector 39 can be used to form the branched fluid flow paths, as between branch tubes 20C; 20D; and 20E.

The assembly 10 shown in FIG. 1, once sterilized, constitutes a sterile, "closed" system, as judged by the applicable standards in the United States. The assembly 10 remains "closed" during processing. This assures that the longest authorized storage intervals can be used for the components collected.

It should be appreciated that, alternatively, the assembly 10 can initially comprise a group of sterile subassemblies. For example, the primary bag 12 could comprise one sterile subassembly, the transfer bag 14 another sterile subassembly, the transfer bag 16 yet another sterile subassembly, and the separation device 40 and transfer bag 18 still another sterile subassembly. In this arrangement (not shown), the branch tubes 20A, 20B, and 20C would carry mating sterile connection devices that the user connects together at time of use, thereby creating the single integral assembly 10 shown in the drawings. Sterile connection devices that could be used for this purpose are shown in Granzow et al. U.S. Pat. Nos. 4,157,723 and 4,265,280.

Figure 6:
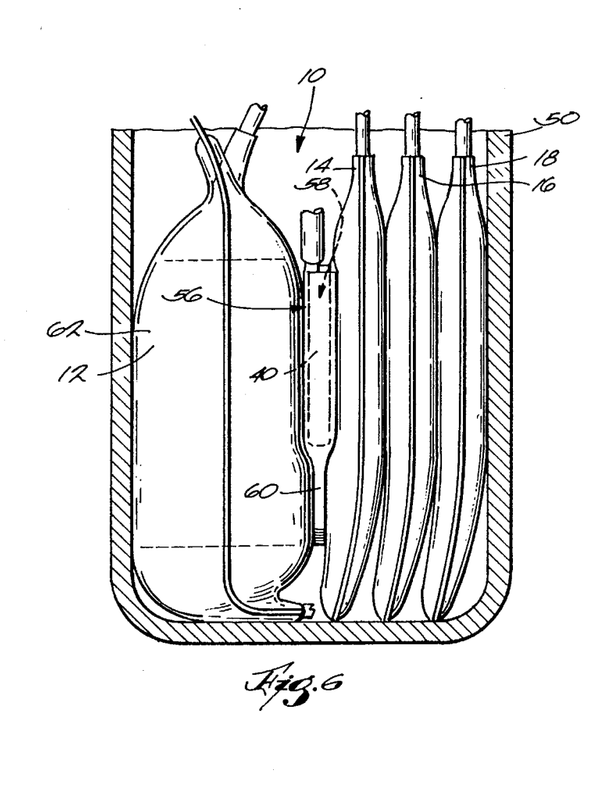
FIG. 6 is a side section view of the assembly shown in FIG. 1 when nested within a centrifuge bucket, showing the integral separation device retained within in a flexible protective pouch.

During the first processing step, whole blood is collected through the donor tube 22 in the primary bag 12 (as FIG. 1 shows). The system 10 is then placed as an integral assembly into a bucket 50 of a conventional blood centrifuge (as FIG. 6 shows).

The bucket 50 is spun at high speeds to centrifugal separate the whole blood within the primary bag 12 into the red blood cell (RBC) component and PRP or PPP plasma component.

Whether the separation process provides PRP or PPP plasma component depends upon the rotational speed and time of processing. Slower rotational speeds over a given time period (called a "soft" spin) produce PPP. Higher rotational speeds over the same time period (called a "hard" spin") yield more platelets in the plasma, produce PRP.

As FIG. 2 shows, the heavier RBC component collects in the bottom of the primary bag 12 during processing. The lighter PRP/PPP plasma component collects at the top of the primary bag 12 during centrifugation.

During centrifugal separation, an intermediate layer of leukocytes (commonly called the "buffy coat" and identified as BC in FIG. 2) forms between the red blood cell component and the PRP/PPP plasma component. If the plasma component is PPP, the buffy coat also includes a substantial amount of platelets. If the plasma component is PRP, substantially fewer of platelets remain in the buffy coat.

Following the centrifugation step, the user removes the system 10 from the centrifuge bucket 50 to begin the second processing step (as FIG. 2 shows). In this step, the user manually breaks the cannulas 26 and 28 open. The primary bag 12 is then compressed or squeezed between two spaced apart plates 52. The compression simultaneously expresses the PPR/PPP component from the top port 38 of the bag 12, while the RBC component is expressed from the bottom port 36 of the bag 12. The buffy coat layer BC remains behind in the bag 12.

Johansson et al U.S. Pat. No. 4,350,585 discloses a system having plates 52 for compressing the primary bag 12 to simultaneously expel plasma and RBC components from the top and bottom ports 36 and 38 of the bag 12. A commercial embodiment of such a system is sold by Baxter Healthcare Corporation (Fenwal Division) under the tradename OPTI-PRESS.

As FIG. 2 shows, while the bag 12 is squeezed by the plates, the PRP/PPP plasma component flows through the tubing branch 20A into the transfer/storage bag 14. At the same time, the RBC component flows through the tubing branch 20B into the transfer bag 16, where it mixes with the storage solution S.

This technique keeps the buffy coat (BC) sandwiched between the PRP/PPP component and RBC component, while these components are expressed from the primary bag 12. This technique retains the buffy coat in the primary bag 12 and, with it, most of the leukocytes for subsequent harvesting or disposal. This technique provides from about 0.75 to about 1.00 log reduction in the number of leukocytes in the PRP/PPP plasma component and RBC component, when compared to the leukocytes contained in the whole blood.

Figure 3:
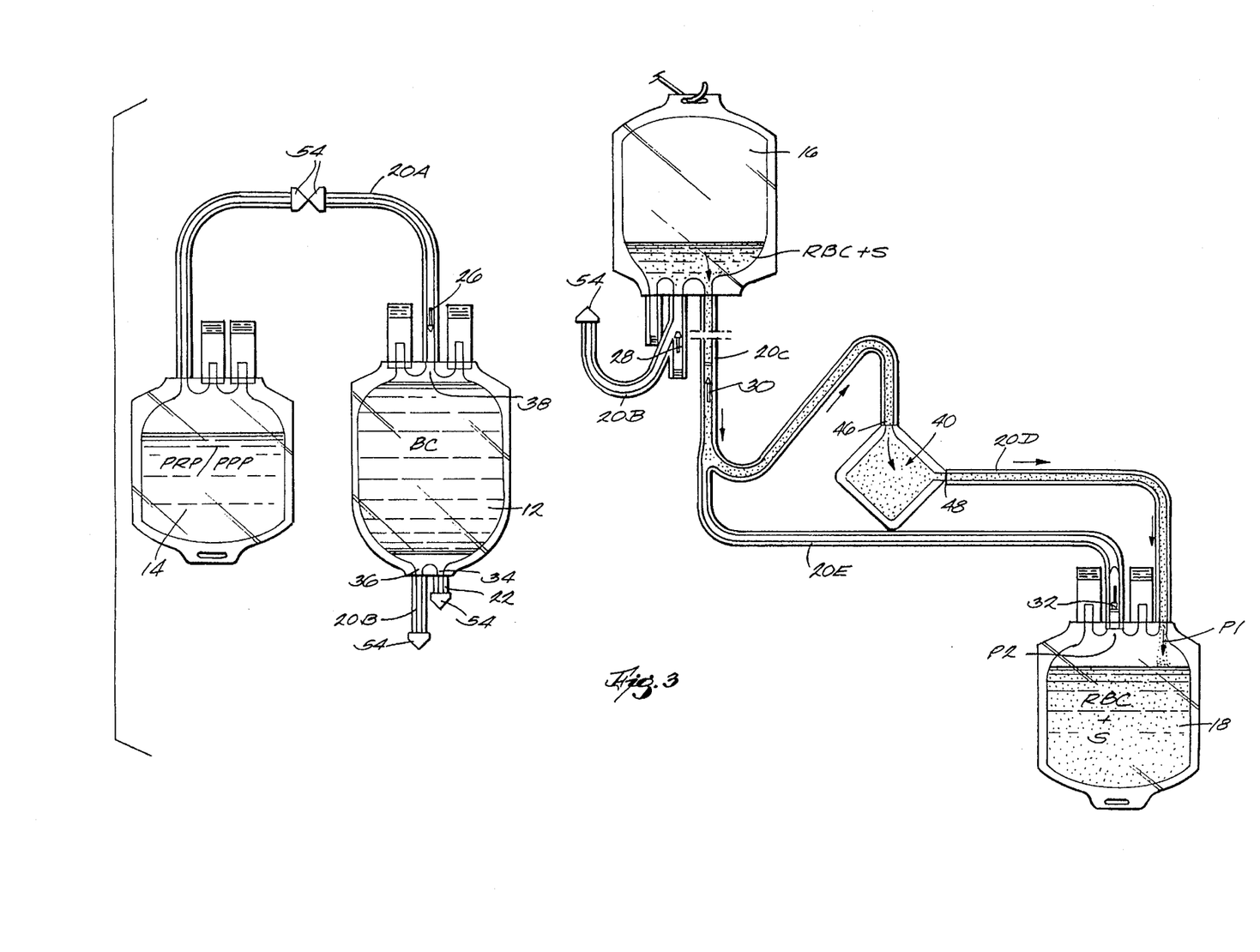
FIG. 3 is a schematic view of the assembly shown in FIG. 1, in which the RBC component is being transferred through a separation device to remove undesired matter from the RBC component, while the plasma component resides in a now-separated transfer bag.

As FIG. 3 shows, at the end of the second processing step, the transfer bag 14 (containing the PRP/PPP component) and the transfer bag 16 (containing the RBC component mixed with storage solution S) can be separated in a sterile fashion from the primary bag 12 (containing the BC component) for independent handling.

The separation of the bags 12; 14; and 16 can be accomplished by forming snap-apart seals 54 in the branch tubes 20A and 20B. A conventional heat sealing device (for example, the Hematron® dielectric sealer sold by Baxter Healthcare Corporation) can be used for this purpose. This device forms a hermetic, snap-apart seal 54 in the branch tubes 20A and 20B.

Preferably, the donor tubing 22 is also sealed and disconnected from the primary bag 12 in the same fashion before centrifugation (as FIGS. 2 and 3 show).

In a third processing step (shown in FIG. 3), the user further manipulates the separated transfer bags 16 and 18, the separation device 40, and interconnecting tube branches 20C; 20D; and 20E.

In this step, the user suspends the transfer bag 16 above the transfer storage bag 18. The user breaks the cannula 30 to open communication between the transfer bag 16 and the transfer/storage bag 18 via the tubing branches 20C and 20D and the separation device 40. The RBC component (mixed with storage solution S) flows by gravity through the separation device 40 into the transfer bag 18 through the port P1.

It should be appreciated that the separation device 40 can be used to remove all types of undesired materials from the RBC component, depending upon its particular construction. In the illustrated embodiment, the separation device 40 is intended to remove leukocytes from the RBC component before storage.

In this arrangement (as FIG. 7 best shows), the separation device 40 includes a housing 42 containing a conventional fibrous filtration medium 44 suited for the removal of white blood cells from red blood cells. The filtration medium 44 can include cotton wool, cellulose acetate or another synthetic fiber like polyester. The undesired matter (i.e., white blood cells) are removed from the RBC component by the separation device 40.

The third processing step thereby supplements the previous separation and compression processes (shown in FIG. 2) in removing leukocytes from the RBC component. The separation device 40 compliments the leukocyte removal efficiencies of the top and bottom port configuration of the primary bag 12. The use of the separation device 40 provides an additional 0.5 to about 1.0 log reduction in the number of leukocytes in the RBC component during processing.

The bag 16, being part of an integral closed system, is not vented to atmosphere. Furthermore, the bag 16 preferably contains only a relatively limited volume of residual air. As the total liquid volume of RBC component (and solution S) drains from the bag 16, and as the limited residual air volume is depleted, the sidewalls of the bag 16 will progressively collapse inward, until flow of the RBC component (and solution S) through the separation device 40 stops. This marks the end of the third processing step.

Figures 4, 5:
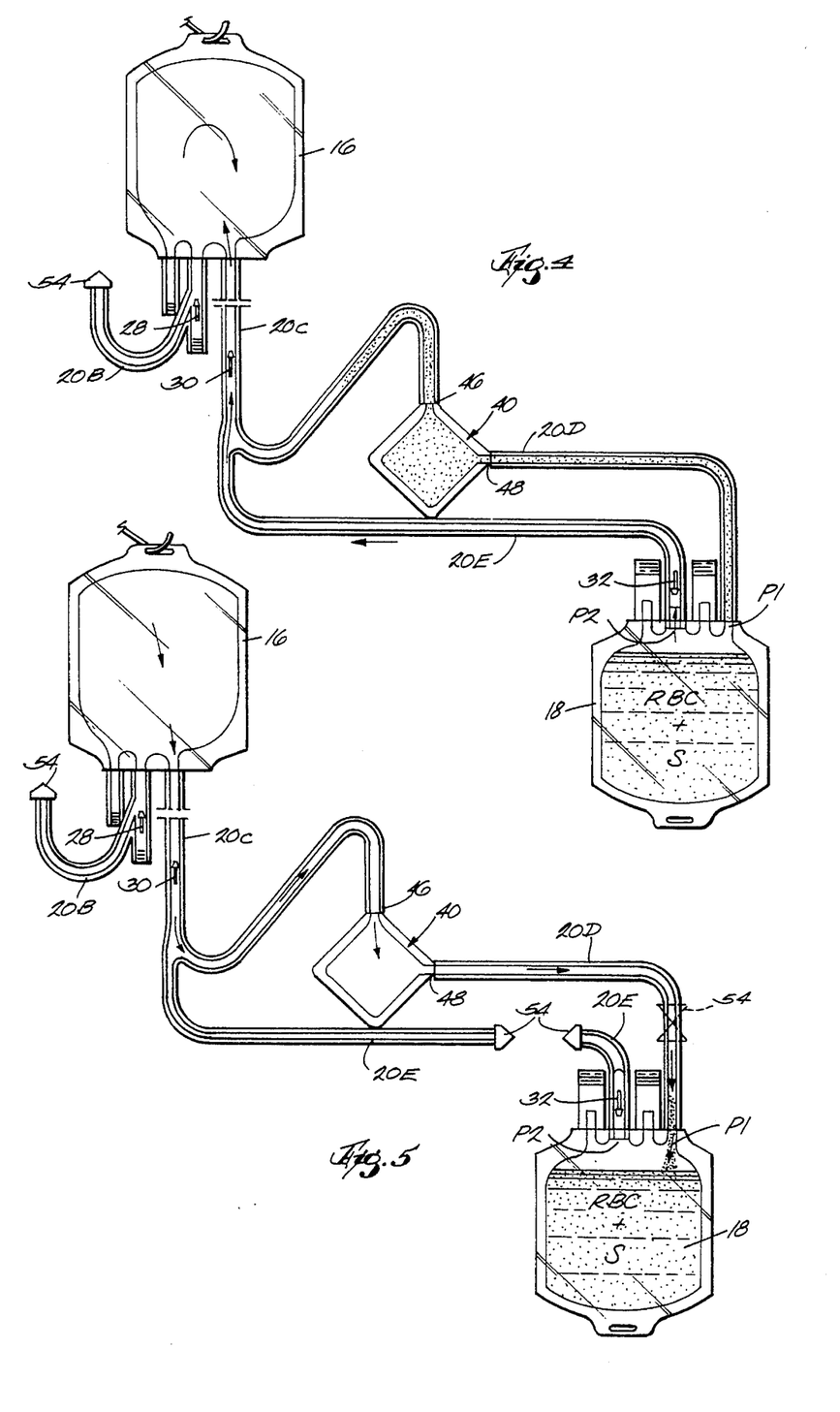
FIG. 4 is a schematic view of a portion of the assembly shown in FIG. 1 when used to vent air from the bag into which RBC component is collected after removal of undesired matter.
FIG. 5 is a schematic view of a portion of the assembly shown in FIG. 1 when using vented air to flush RBC component from the separation device that removes undesired matter.

As FIG. 4 shows, the cessation of flow ending the third processing step normally traps a residual volume of the RBC component (and solution S) within the separation device 40 and in the portions of the tube branch 20D upstream and downstream of the separation device 40. This residual volume diminishes the overall amount of RBC component available for storage and therapeutic use.

Furthermore, in a typical system, the transfer/storage bag 18 contains about 40 cubic centimeters of residual air by the end of the third processing step. About 20 cubic centimeters of the air is initially present in the transfer/storage bag 18 before receiving the RBC component. The transfer of the RBC component (and solution S) from the bag 16 through the tube branches 20C and 20D and the separation device 40 displaces about 20 more cubic centimeters of residual air into the transfer bag 18. It is desirable to rid the transfer/storage bag 18 of this residual air before long term storage of the RBC component.

The assembly 10 includes a fourth processing step to vent residual air from the transfer/storage bag 18. The assembly 10 also includes a fifth processing step to direct the residual air to move the trapped residual volume of RBC component (and solution S) into the transfer/storage bag 18.

In the fourth processing step (as FIG. 4 shows), the user opens the cannula 32. The user gently squeezes the bag 18 to vents the residual air entrapped in the transfer bag 18 through the branch tube 20E through a second port P2, separate from the first port P1. The residual air flows through the second port P2 and into the branch tube 20E while the residual volume of RBC component (and solution S) occupy the separation device 40.

The branch tube 20E directs the residual air out of the bag 18 through the port P2 around the separation device 40 into the tube branch 20C. The vented air, following the path of least flow resistance, enters the bag 16. The residual air vented from the bag 18 collects in the bag 16.

In a fifth processing step (as FIG. 5 shows), the user forms a snap-apart seal 54 in the branch tube 20E upstream of the cannula 32. This closes the branch tube 20E while separating the transfer/storage bag 18 from the branch tube 20E.

The expelled residual air volume transferred into the bag 16 enters the branch tubes 20C and 20D, which are the only remaining paths open to flow communicating with the bag 16. The residual air volume will displace all or at least a significant part of the residual volume of RBC component (and mixed solution S) in the tube branch 20D and separation device 40. The freed residual volume of RBC component (and solution S) flows into the transfer/storage bag 18.

The assembly 10 therefore vents residual air from the bag 18 through the second port P2, collecting the vented air in the bag 16. The residual air is vented through a port (port P2) and a path (branch 20E) that not only bypass the separation device 40, but that are also kept free from contact with blood throughout the blood separation and collection process.

The assembly 10 then circulates the vented air from the bag 16, back toward the inlet of the separation device 40. The vented air displaces residual RBC component (and solution S) from the separation device 40 and inline flow branch tube 20D, causing it to flow into the bag 18 through the port P1 for storage.

The transfer/storage bag 18 can now be separated from the branch tube 20D by forming a snap-apart seal 54 (shown in phantom lines in FIG. 5) for subsequent storage of the filtered RBC component/solution S mixture.

After separating the transfer/storage bag 18 from the branch tube 20D, the user preferably gently squeezes the bag 18 to uniformly mix the RBC blood component in the bag 18. Mixing is preferred at this step of the process, because it has been observed that the residual volume of RBC component often contains a larger concentration of leukocytes (albeit a small concentration) than the preceding volumes. Mixing makes uniform the remaining small concentration of leukocytes in the RBC component (and solution S) during storage.

Figure 5A:
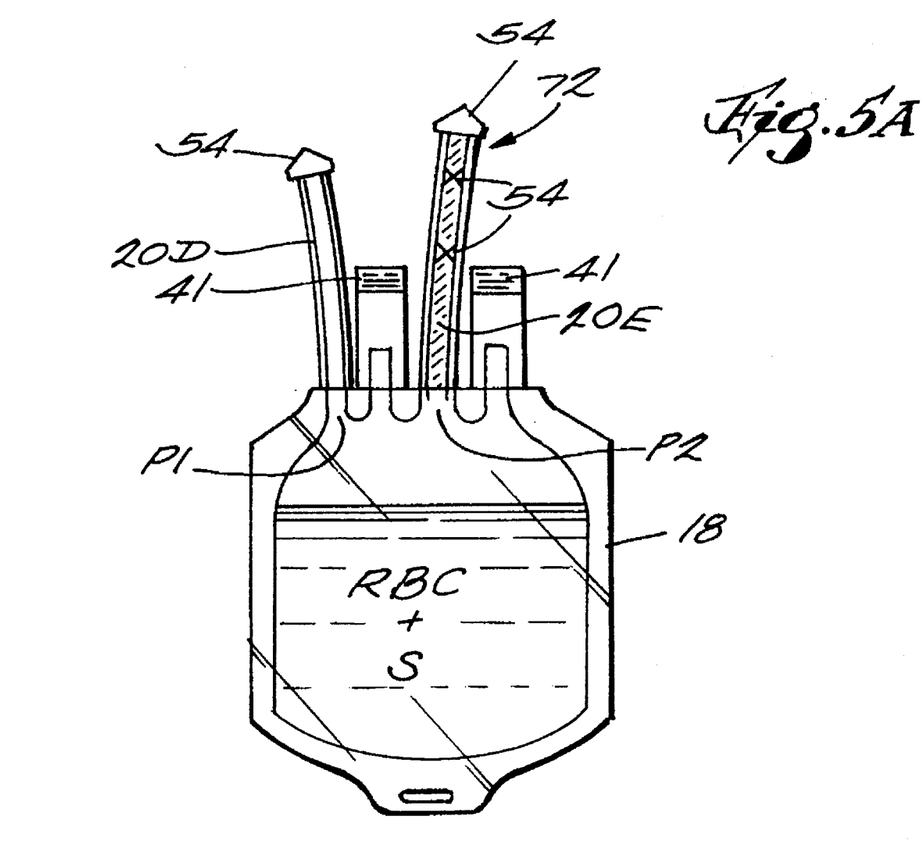
FIG. 5A is a schematic view of the RBC component collection container, with integral sample tube formed from the air vent path.

As FIG. 5A shows, the sealed portion of the air vent branch tube 20E that remains attached to the bag 18 (via the port P2) can serve as a sample tube 72. Using a convention blood tube stripper, the user displaces the residual air from the tube 72 and into the bag 18. An aliquot of the RBC component (and solution S) will fill the tube 72 through the port P2. The user then uses a conventional heat sealing device (for example, the Hematron® dielectric sealer) to form one or more hermetic, snap-apart seals 54 spaced apart along the length of the tube 72.

The sample tube 72 retains one or more small aliquots or samples of the collected blood. The sample(s) are used to later crossmatch and type the donor's blood before transfusing the collected RBC component. The tube 72, integrally attached to the bag 18, preserves a direct link between the donor's blood sample and the RBC component stored in the bag 18.

According to this aspect of the invention, the assembly 10 retains the blood sample in a portion of tubing (i.e., a portion of the branch tube 20E) that beforehand serves only to transfer air, and is thereby kept free of prior contact with blood. The assembly 10 thus eliminates the chance of contaminating the relatively small blood sample in the sample tube 72 with a disproportionately large number of leukocytes, such as might be present in the branch tube 20D in the later stages of processing, as earlier discussed.

In the assembly 10 shown in FIG. 1, the separation device 40 remains integrally attached to the assembly 10 during the centrifugation process. As FIG. 6 shows, during centrifugation, the separation device 40 occupies the blood centrifuge bucket 50 alongside the bags 12; 14; 16; and 18.

Typically (as FIG. 6 shows), the primary bag 12 nests against one side of the bucket, and the other bags 14; 16; and 18 nest in succession against the other side. In this arrangement, the separation device 40 is sandwiched within the bucket 50 next to the primary bag 18.

In the illustrated and preferred embodiment (see FIGS. 6 and 7), the separation device 40 is housed within a flexible pouch 56 during centrifugation within the bucket 50. The pouch 56 includes a pocket 58 that receives the separation device 40 in a snug fit during processing.

The pouch 56 preferably presents a relatively thin, flat profile, as FIG. 6 best shows. It thereby does not significantly add to the volume and weight of items carried within the bucket 50.

The pouch 56 is preferably made of a generally flexible material. The durometer and thickness of the material is selected to present a relatively flat profile that resists major deflection.

In one preferred embodiment, the pouch 56 is made from a medical grade plastic material, like PL-742® plastic material. It can also be made of an elastomeric material, like silicone rubber.

The pouch 56 can be made by gluing a flat sheet of plastic or elastomeric material into the desired configuration. Alternatively, the pouch 56 can be made by injection molding.

When placed within the bucket, the pouch 56 creates a soft yet relatively stiff interface between the separation device 40 and the adjacent bags 12; 14; 16; and 18 within the bucket. By enclosing the separation device 40 within the soft pocket 58, the pouch 56 shields the bags in the bucket 50 from direct contact against the separation device 40 during centrifugation. In this way, the pouch protects the bags from puncture or damage during processing.

Figure 7:
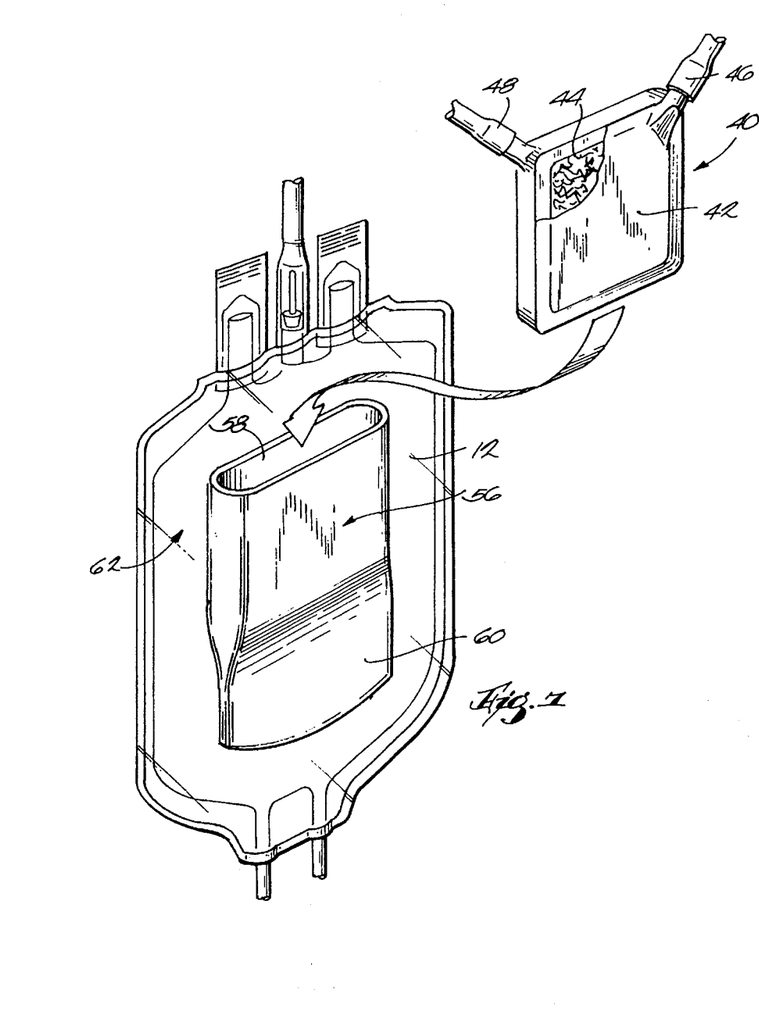
FIG. 7 is an exploded perspective view of the separation device and the flexible protective pouch, when nested against the primary bag, as would occur within the centrifuge bucket shown in FIG. 6.

As FIG. 7 best shows, the pouch 56 can also includes an elongated tail section 60 that extends below the pocket 58. In this configuration, the pouch 56 presents in overall width and height a surface area that covers a substantial portion of the effective separation zone 62 of the primary bag 12, when laid against it, as FIG. 7 shows.

In this arrangement, the pouch 56, when nested against the separation zone 62, serves to resist deformation of the zone 62 in response the strong centrifugal forces present in the bucket 50 during processing.

In the illustrated embodiment, the pouch 56 measures about 3.0 inches in width, about 5.0 inches in maximum height. Its side wall has a thickness of about 1/16 inch in the region of the pocket 58 and a thickness of about 1/8 inch in the region of the tail section.

The pouch 56 having these dimension will cover a substantial portion of the separation zone of a typical 450 ml primary bag. A bag of this size has an effective separation zone 62 with a height of about 6 inches and a width of about 4¾ inches.

Figure 8:
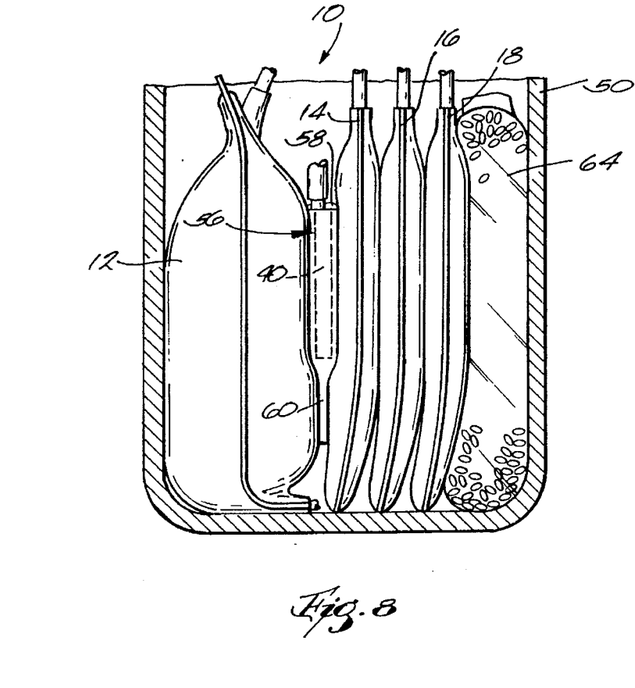
FIG. 8 is a side section view of the assembly shown in FIG. 1 when nested within a centrifuge bucket, in which the separation device is retained in a protective pouch, and in which a ballast bag is used to fill an empty region in the bucket.

During processing, one or more ballast bags 64 may be required to fill empty areas in the centrifuge bucket 50 not occupied by the assembly 10, as FIG. 8 shows.

In the illustrated embodiment, the ballast bag 64 includes sidewalls 66 made of a flexible medical grade plastic material, like plasticized PVC. The sidewalls 66 enclose an open interior volume 68. Hard plastic pellets 70 occupy about one-third to one-half of the interior volume 68.

Various modifications of the invention will be apparent to those skilled in the art within the purview of the following claims.

We claim:

1. A blood processing assembly comprising a first container having a first port and a second port different than the first port, a sample tube communicating with the second port and not the first port, a second container including means for receiving blood from a source, the second container holding an additive solution for mixing with the received blood, separation means for separating undesired matter from blood, the separation means having an inlet communicating with the second container and an outlet communicating with the first port and not the second port of the first container, means for directing blood mixed with additive solution from the second container through the separation means inlet for removing undesired matter while directing the blood mixed with additive solution and substantially free of undesired matter from the separation means outlet into the first port and not the second port of the first container to keep the second port essentially free of blood contact while the separation means removes undesired matter from blood mixed with additive solution in the second container, means for expelling residual air from second port of the first container into the second container, means for directing the residual air from the second container toward the inlet of the separation means to move residual blood mixed with additive solution from the separation means for collection in the first container through the first port and not the second port to keep the second port essentially free of contact with residual blood mixed with additive solution moved by residual air from the separation means, and means for selectively directing a sample of blood essentially free of undesired matter from the first container through the second port into the sample tube.

2. A method for processing blood using a collection container that has a first port and a second port different than the first port comprising the steps of directing blood through an inlet of a separation device for removing undesired matter while directing the blood substantially free of undesired matter from an outlet of the separation device and into the collection container through the first port and not the second port to keep the second port free of blood contact while the separation device removes undesired matter, expelling residual air from the collection container through a tube attached to the second port and not the first port, directing the residual air in the tube toward the inlet of the separation device to move residual blood from the separation device for collection in the collection container through the first port and not the second port to keep the second port and the tube essentially free of contact with residual blood moved by residual air from the separation device, after expelling residual air from the collection container through the second port and tube, sealing the tube at a location remote from the second port, and transferring a sample of the blood from the collection container into the tube through the second port.

3. A method according to claim 2 wherein, in the step of directing the blood through the separation device, leukocytes are removed from the blood.

4. A method according to claim 2 wherein, in the step of directing the blood through the separation device, leukocytes are removed from the blood by filtration.

5. A method according to claim 2 and further including the step of collecting the residual air expelled from the collection container, and wherein, in the step of directing the residual air toward the separation device inlet, it is the stored residual air that is directed.

6. A blood processing assembly comprising a container having a first port and a second port different than the first port, a separator to remove undesired matter from blood, the separator having an inlet and an outlet, a first tubing path attached to the separator inlet, a second tubing path attached to the separator outlet and the first port and not the second port, a third tubing path attached to the second port and not the first port and communicating with the first tubing path, and flow control means operable in conjunction with the first, second, and third tubing paths (i) in a first mode for directing blood through the first tubing path and not the third tubing path through the separator inlet to remove undesired matter while directing blood substantially free of undesired matter from the separator outlet through the second tubing path into the container through the first port and not through the second port, thereby keeping the second port and the third tubing path essentially free of blood contact while the separator removed undesired matter, (ii) in a second mode for directing residual air from the container through the second port and the third tubing path, into the first tubing path and the separator inlet to move residual blood from the separator through the separator outlet and second tubing path into the container through the first port and not through the second port, the second port and the third tubing path thereby remaining essentially free of contact with residual blood moved by residual air from the separator, and (iii) after residual air from the container moves residual blood from the separator during the second mode, in a third mode for transferring a sample of blood, essentially free of undesired matter, from the container into the third tubing path through the second port and not through the first port.

7. A blood processing assembly comprising a first container having a first port and a second port different than the first port, a sample tube communicating with the second port and not the first port, a second container including means for receiving blood from a source, separation means for separating undesired matter from blood, the separation means having an inlet communicating with the second container and an outlet communicating with the first port and not the second port of the first container, means for directing blood from the second container through the separation means inlet for removing undesired matter while directing the blood substantially free of undesired matter from the separation means outlet into the first port and not the second port of the first container to keep the second port essentially free of blood contact while the separation means removes undesired matter, means for expelling residual air from second port of the first container into the second container, means for directing the residual air from the second container toward the inlet of the separation means to move residual blood from the separation means for collection in the first container through the first port and not the second port to thereby keep the second port essentially free of contact with residual blood moved by residual air from the separation means, and means for selectively directing a sample of blood essentially free of undesired matter from the first container through the second port into the sample tube.

* * * * *

UNITED STATES PATENT AND TRADEMARK OFFICE
CERTIFICATE OF CORRECTION

PATENT NO.    : 5,527,472
DATED         : June 18, 1996
INVENTOR(S)   : Marc Bellotti et al.

It is certified that error appears in the above-identified patent and that said Letters Patent is hereby corrected as shown below:

Column 3, Line 44   Delete "centrifuges" and substitute --- centrifuge ---
Column 3, Line 54   Before "system" insert --- the ---
Column 5, Line 21   After "alternatively," delete "the"
Column 6, Line 44   Delete "centrifugal" and substitute --- centrifugally ---
Column 8, Line 50   Delete "vents" and substitute --- vent ---
Column 10, Line 29  Delete "includes" and substitute --- include ---
Column 10, Line 37  After "response" insert --- to ---
Column 10, Line 45  Delete "dimension" and substitute --- dimensions ---

Signed and Sealed this

Twenty-third Day of June, 1998

Attest:

BRUCE LEHMAN

Attesting Officer    Commissioner of Patents and Trademarks